(12) United States Patent
DeCourcy et al.

(10) Patent No.: US 7,723,541 B2
(45) Date of Patent: May 25, 2010

(54) PROCESS FOR MANUFACTURING HIGH PURITY METHACRYLIC ACID

(75) Inventors: Michael Stanley DeCourcy, Houston, TX (US); James Edward Elder, Houston, TX (US); Jamie Jerrick John Juliette, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 483 days.

(21) Appl. No.: 11/521,744

(22) Filed: Sep. 15, 2006

(65) Prior Publication Data

US 2007/0010690 A1 Jan. 11, 2007

Related U.S. Application Data

(62) Division of application No. 10/855,034, filed on May 27, 2004, now abandoned.

(60) Provisional application No. 60/483,703, filed on Jun. 30, 2003.

(51) Int. Cl.
*C07C 57/02* (2006.01)
*C07C 51/08* (2006.01)

(52) U.S. Cl. ...................... 562/598; 562/599

(58) Field of Classification Search ........................ None
See application file for complete search history.

(56) References Cited

U.S. PATENT DOCUMENTS

| 2,283,991 | A |   | 5/1942  | Hill |
|-----------|---|---|---------|------|
| 3,264,272 | A |   | 8/1966  | Rees et al. |
| 3,562,320 | A | * | 2/1971  | Woodward et al. .......... 562/599 |
| 4,199,410 | A |   | 4/1980  | Ohrui et al. |
| 4,351,931 | A |   | 9/1982  | Armitage |
| 5,002,979 | A |   | 3/1991  | Stoyan |
| 5,948,874 | A |   | 9/1999  | Pike et al. |
| 5,973,046 | A |   | 10/1999 | Chen et al. |
| 6,310,163 | B1|   | 10/2001 | Brookhart et al. |
| 2002/0156220 | A1 | | 10/2002 | Meyer et al. |
| 2003/0028071 | A1 | | 2/2003  | Handy et al. |
| 2003/0205451 | A1 | | 11/2003 | Briegel et al. |

FOREIGN PATENT DOCUMENTS

| EP | 1361203    |   | 1/1983 |
| EP | 1125912    | A | 8/2001 |
| EP | 1361203    | A | 11/2003 |
| JP | 2001226318 |   | 8/2001 |

OTHER PUBLICATIONS

"Standard Specification for Glacial Methacrylic Acid", D3845-96(2000)ASTM.
"Glacial Methacrylic Acid" Technical Information, TI/ED 1655, Feb. 2002 BASF Aktiengesellschaft, Ludwigshafer, Germany.
"Methacrylic Acid, Glacial", Technical Data Sheet, Jan. 1997, Industrial Inorganics, BASF Corporation, Mount Olive, New Jersey.

* cited by examiner

*Primary Examiner*—Paul A Zucker
(74) *Attorney, Agent, or Firm*—Marcella M. Bodner (57) ABSTRACT

A process is provided herein for the high yield production of high purity glacial methacrylic acid ("HPMAA") that is substantially pure, specifically 99% pure or greater, with water content of 0.05% or less and low levels of other impurities, including HIBA, acrylic acid, MOMPA, methacrolein and others. This improved process comprises providing a crude MAA stream and purifying the crude methacrylic acid stream in a series of successive distillation steps involving two distillation columns. The inventive process is capable producing high purity methacrylic acid product that is especially suitable for the production of specialty MAA polymers.

3 Claims, 3 Drawing Sheets

PROCESS FOR MANUFACTURING HIGH PURITY METHACRYLIC ACID

This non-provisional application is a divisional of non-provisional U.S. patent application Ser. No. 10/855,034, filed May 27, 2004, now abandoned, benefit of which is claimed under 35 U.S.C. § 120 and which In turn claims benefit under 35U.S.C. § 119(e) of U.S. provisional Application No. 60/483,703, filed Jun. 30, 2003, priority benefit of which is also claimed for the present application.

The present invention is related to a process for the production of substantially pure ethacrylic acid having at least 99 weight % methacrylic acid, 0.05 weight % or less water, and specified reduced amounts of other impurities compared to other grades of methacrylic acid. More specifically, the substantially pure methacrylic acid produced by the process of the present invention is suitable for use as a feedstock for certain specialty polymers.

Methacrylic acid ("MAA") is used in a wide variety of applications. Typical end-use applications include: acrylic plastic sheeting; molding resins; polyvinyl chloride modifiers; processing aids; acrylic lacquers; floor polishes; sealants; auto transmission fluids; crankcase oil modifiers; automotive coatings; ion exchange resins; cement modifiers; water treatment polymers; electronic adhesives; metal coatings; and acrylic fibers. MAA is especially prized in these applications and others because of the hardness it imparts to the products in which it is used. MAA also enhances chemical stability and light stability, as well as ultraviolet radiation resistance, of the products in which it is used. Therefore, MAA is often used in applications requiring resins of excellent transparency, strength, and outdoor durability. The MAA market is extremely cost-sensitive; thus, any improvement in process yield, however slight, can result in significant market advantage.

Unpurified MAA generally has impurity levels of about 5% or greater and is herein referred to as "crude methacrylic acid" or "crude MAA." Impurities in MAA may comprise one or more of: water, acetic acid, acrylic acid, acetone, methacrolein, acrolein, isobutyric acid, 2-hydroxyisobutyric acid (HIBA), mesityl oxide, 3-methacryloxy-2-methylpropionic acid ("MOMPA", also known as methacrylic acid dimer), methylmethacrylate, propionic acid, and methacrylamide. The presence of specific impurities in the unpurified crude methacrylic acid is dependent at least in part on the production process employed to produce the original crude methacrylic acid.

For example, if the crude methacrylic acid is derived from the reaction of acetone cyanohydrin and sulfuric acid to form methacrylamide (MAM) intermediate, the MAM intermediate then further reacted with water to form methacrylic acid, (referred to herein as an "ACH process"), impurities such as HIBA, methacrylamide, and water would typically be present.

Alternatively, if the crude methacrylic acid is derived from the catalytic gas phase oxidation of one or more raw material gases selected from the list including butylene, isobutylene, butane, iso-butane, t-butyl alcohol, or methacrolein (referred to herein as a "C-4 process"), impurities such as methacrolein, acrolein, and water would typically be present.

Impurities present in MAA can have a negative impact on some of the fundamental properties of the end-use applications of MAA. Accordingly, MAA that has a very low percentage by weight of impurities is very desirable.

Purified MAA having an impurity level of less than 5% by weight is referred to herein as glacial methacrylic acid ("GMAA"). Commercially available GMAA product typically has a methacrylic acid content of about 98.5 to 99.5 wt %, a water content of about 0.2 to 0.3 wt %, and a product color of about 20 to 25 APHA (i.e., the color measurement standard established by the American Public Health Association) (see, for example, "Standard Specification for Glacial Methacrylic Acid", D3845-96 (2000), ASTM and "Glacial Methacrylic Acid" Technical Information, TI/ED 1655 e February 2002, BASF Aktiengesellschaft).

It will be apparent to one of ordinary skill in the art, however, that although not identified in product specifications, commercial GMAA must additionally contain impurities other than water, such unspecified impurities being responsible for the high product color (i.e., APHA value) of commercial GMAA. These unspecified impurities may include compounds such as those described above, which are commonly found in unpurified crude MAA. Because processes for producing GMAA do not consistently control impurities other than water, it is not surprising that the concentration of such impurities is not identified in the product specifications for commercial GMAA.

Purified MAA having an impurity level of not more than 1% by weight wherein no more than 0.05% by weight is water is referred to herein as high purity glacial methacrylic acid ("HPMAA"). Although HPMAA is a desirable product, it is costly to produce.

A three-column distillation process for producing HPMAA from crude methacrylic acid is described in co-pending United States application U.S. Ser. No. 10/420,273 filed Apr. 22, 2003. Producers of HPMAA would greatly welcome improvements in the production of HPMAA that could further lower capital and operating costs. Therefore, there is an unaddressed need for a method to produce HPMAA at a reduced cost for the manufacturer.

With its low water content, HPMAA is suitable as a feedstock in the manufacture of specialty polymers comprising MAA, herein referred to as "specialty MAA polymers". Representative examples of specialty MAA polymers and their methods of manufacture are provided, in U.S. Pat. No. 5,002,979; US 2003/0028071; US 2002/0156220; U.S. Pat. No. 4,351,931; U.S. Pat. No. 5,973,046; and U.S. Pat. No. 3,264,272.

In many specialty MAA polymer processes, the presence of water is particularly detrimental for the formation and composition of the polymer end product. Therefore it is common for specialty MAA polymer producers to treat the raw material monomers to remove any residual traces of water. For example, in anionic polymerizations, water can act as a chain terminator and in polymerization processes based on diimine catalysts (e.g., U.S. Pat. No. 6,310,163) water may interfere with the catalyst itself. Common treatment methods include passing the monomer through neutral alumina or drying the monomer over molecular sieves. Such additional purification steps, however, add unwanted cost and complexity to specialty MAA polymer production. This cost is increased in cases where the monomer contains a high concentration of water. It will be evident, therefore, that any reduction in the water level of the raw material monomer, even if the water content cannot be reduced to zero, will beneficially impact the polymer production process by reducing the extent and associated cost of such treatment steps. Impurities, other than water, that may be present in methacrylic acid, including GMAA, can also have a detrimental effect on the production of specialty MAA polymers.

For example, organic impurities that may be present in MAA, such as acetic acid and aldehydes (e.g., methacrolein), can act as undesired chain transfer agents during specialty MAA polymer preparation. Other organic impurities, such as the dimer of MAA (MOMPA) and methylmethacrylate, may become incorporated into the polymer molecule, leading to undesired changes in the polymer's properties.

Of the potential organic impurities in methacrylic acid the presence of HIBA is particularly problematic to the preparation of specialty polymers. The HIBA dimer can cyclize to produce 3,3,6,6-tetramethyl-1, 4-dioxane-2, 5-dione (also known as tetramethylglycollide). Incorporation of tetramethylglycollide into a polymer chain lowers the resistance of the final specialty polymer to acids and bases—a result which is particularly undesirable in ethylene-MAA ("E-MAA") copolymers. The dimerization and cyclization of HIBA also generates water in-situ that further complicates the polymer production process.

HIBA in methacrylic acid may also undergo acid catalyzed decomposition, during specialty MAA polymer preparation processes, to form decomposition products, including water, acetone, and carbon monoxide, thereby altering the structure and molecular weight of the polymer end product. This water-forming reaction would be especially problematic, for example, in a process where methacrylic acid is used as the solvent for a strong acid catalyst (e.g., U.S. Pat. No. 5,948,874).

Thus it will be evident to one of ordinary skill in the art that impurities present in methacrylic acid can have significant negative impacts on specialty MAA polymer properties such as melt index, transparency, or resistance to acidity. In some cases, the presence of impurities may make the polymer unsuitable for a specific application, such as in-vivo use of a non-bioreactive or ocular-compatible polymer. In other cases, the impact of undesired impurities may be evident only after further processing, such as during or after compounding of the specialty MAA polymer with other materials.

Accordingly, there is also an unaddressed need to produce a high purity methacrylic acid product that is especially suitable for the production of specialty MAA polymers. Given that even minor reductions in product methacrylic acid impurity levels can have significant positive effects on the quality and production cost of specialty MAA polymers, producers of specialty MAA polymers would greatly welcome the advent of an improved process for purifying crude Methacrylic acid, capable of producing methacrylic acid product with impurity levels even lower than typical HPMAA specifications.

The purification process of the present invention may be used to remove undesirable impurities from crude methacrylic acid, thereby economically producing HPMAA, as well as grades of MAA with minimal impurity levels that are especially desirable for use in specialty MAA polymer production.

BRIEF DESCRIPTION OF THE DRAWINGS

Objects, features and advantages of the present invention will be apparent from the following description of some embodiments of the invention. These embodiments are given for the purpose of disclosure and may be considered in conjunction with the accompanying drawings. A more complete understanding of the present embodiments and advantages thereof may be acquired by referring to the following description taken in conjunction with the accompanying drawings, in which like reference numbers indicate like features, and wherein.

DETAILED DESCRIPTION

The present invention provides a novel and economical process for producing HPMAA. The present invention involves the purification of crude MAA, or other commercial grades of MAA, to HPMAA via the use of distillation columns to remove various impurities (generally, light impurities, heavy impurities, and water) from an MAA stream such that the resultant product is substantially purified methacrylic acid. More particularly, the substantially purified methacrylic acid, HPMAA, is at least 99% pure MAA having not more than 0.05 wt% water, based on the total weight of the HPMAA. The improved process of the present invention comprises a two-column distillation system in which capital investment is reduced and operating complexity is minimized. The operating cost is therefore also reduced. The improved process of the present invention is also capable of operation in a manner that will produce methacrylic acid that exceeds the purity specifications for typical HPMAA, thereby providing methacrylic acid that is especially beneficial for use in the preparation of specialty MAA polymers.

As previously noted, eliminating impurities from MAA to produce HPMAA enhances the function of the MAA as a precursor to end use applications of specialty MAA polymers. Some of the characteristics attributable to HPMAA include low color (APHA value), resistance to the effects of acidic or basic substances, and the ability to control the reaction temperature of polymers. HPMAA also should not interfere with the function or operation of catalysts used during specialty MAA polymer production. Many end-use applications of specialty MAA polymers, such as films and contact lenses, also require uniformity of color or a high-degree of transparency. Low color MAA is also preferred when making E-MAA copolymers, especially when the objective is to produce ionomers, where transparency is often a key feature. Additionally, because color generally increases with increasing impurity levels, the color of the methacrylic acid product is indicative of its relative purity. For this reason, specialty MAA polymer producers would find it desirable to utilize raw material methacrylic acid with low color, that is, the product color measures not more than 20 APHA, for example, less than 15 APHA, or less than 10 APHA. The product color measurement may be as low as 5 APHA, or even less. The process of the present invention produces product methacrylic acid with low color and low-levels of impurities such as, but not limited to, acetic acid, acrylic acid, aldehydes, HIBA, MOMPA, methylmetacrylate, acetone, and water.

For clarity, the following definitions are used herein: "top" is the vapor space existing at the extreme top of a distillation column; "bottom" is the liquid sump existing at the extreme bottom of a distillation column; "upper section" is the approximate uppermost ⅓ of the distillation column which is below and adjacent to the "top"; "lower section" is the approximate lowermost ⅓ of the distillation column which is above and adjacent to the "bottom"; "middle section" is the approximate ⅓ of the distillation column intermediate the "upper section" and the "lower section"; "line" is a fluidic connection for transporting vapor and/or liquid into a unit, out of a unit or between two or more units, and may include such common peripherals as valves, condensers, flow meters, etc.

Figure 1:
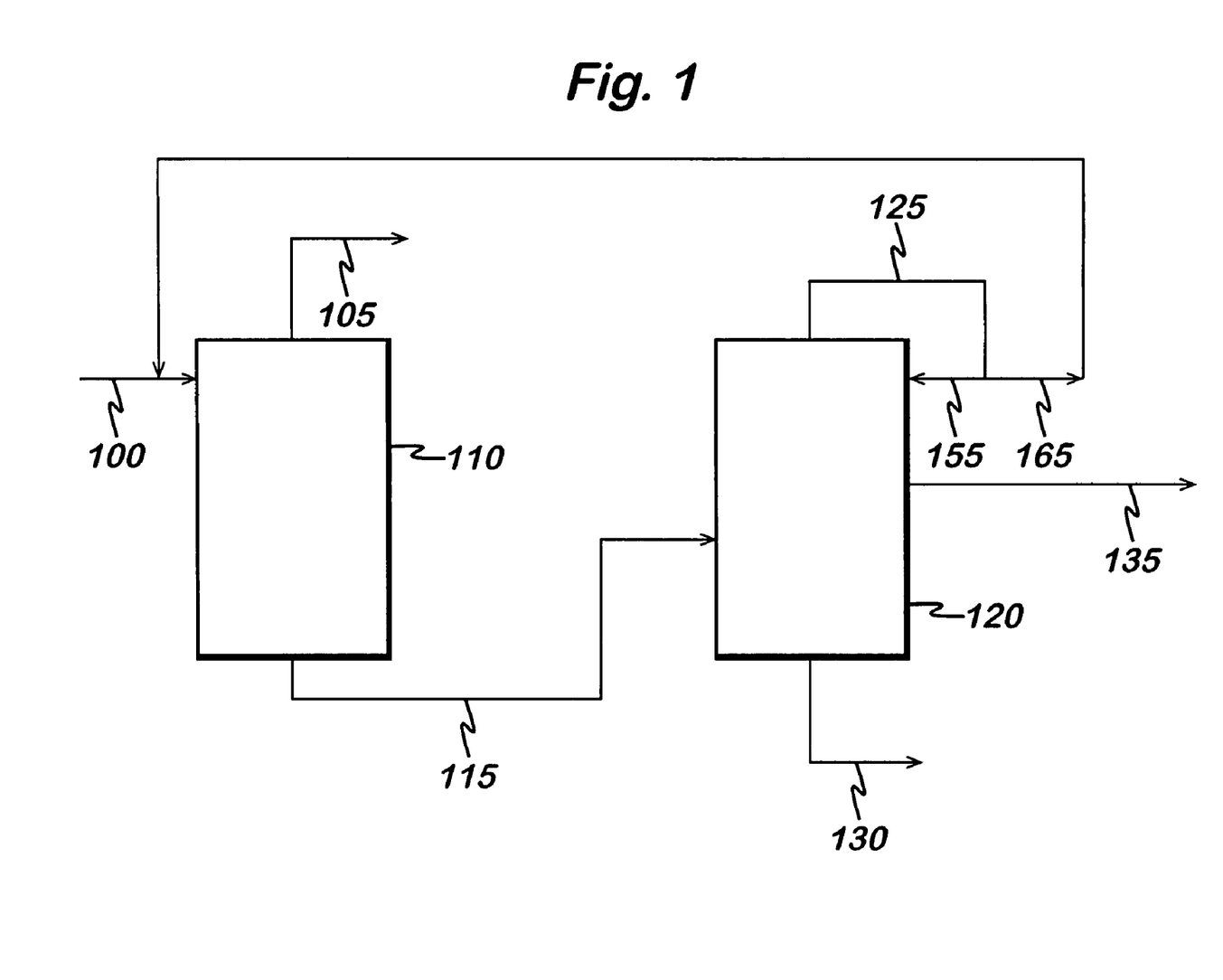
FIG. 1 is a schematic flow diagram of one embodiment of the process for producing HPMAA in accordance with the present invention.

One embodiment of the present invention is illustrated in FIG. 1 and utilizes two distillation columns. In this embodiment, a crude MAA stream 100 is provided to the first of the two distillation columns, HPMAA light ends column 110. Crude MAA stream 100 can be any stream comprising methacrylic acid that requires purification, including, for example, a crude MAA stream originating from an ACH-process or a crude MAA stream originating from a C-4 process, or a partially purified, commercial grade MAA stream originating from another purification process. In light ends column 110, light impurities produced in the crude MAA production process are separated from the MAA, and are removed from light ends column 110 as light ends overhead stream 105. The exact composition of light ends overhead stream 105 varies depending on the specific source of the crude MAA. With regard to the process shown in FIG. 1, the light ends overhead stream 105 comprises one or more components including, but not limited to, acetone, water, acetic acid, acrylic acid, methacrolein, and acrolein. HPMAA light ends column 110 also includes column ancillaries (not shown), wherein the term "column ancillaries" means any and all secondary equipment and associated piping that is connected to a column, such as vacuum equipment, reboilers, condensers, pumps, and process lines including but not limited to feed lines, bottoms lines, overhead lines, vent lines, inhibitor addition lines, oxygen addition lines, reflux lines, and rundown lines, such as are well known by persons of ordinary skill in the art.

HPMAA light ends column 110 and its column ancillaries are preferably constructed of materials resistant to corrosion. Suitable materials of construction resistant to corrosive effects include but are not limited to: 300 series stainless steel, 904L, 6-moly stainless steel, HASTELLOY® (e.g., B, B-2, B-3, C-22, and C-276), tantalum, and zirconium. In some embodiments, the manufacturer may reduce construction costs by utilizing covered base metals. "Covered base metal" materials are materials that are generally thought not to be corrosion resistant, such as carbon steel, combined with a covering thereon, which is capable of resisting corrosion such as glass, epoxy, elastomer, fluoropolymer (e.g., TEFLON®), or one of the above-listed corrosion resistant metals. Covered base metals are constructed by placing a covering capable of resisting corrosion over, and optionally bonding the covering to, the base metal. The covering prevents contact between the base metal and the process stream. Covered base-metal construction is especially preferred for large-diameter piping (3.8 cm or larger nominal diameter) and for heat exchanger tubes in high fluid-velocity service (fluid velocity of 0.15 meter/second or more) and other components, where significant metal thickness (3 mm or more metal thickness) may be used to provide structural strength. The materials described above such as 300 series stainless steel, 904L, 6-moly stainless steel, HASTELLOY® (e.g., B, B-2, B-3, C-22, and C-276), tantalum, zirconium, and covered base-metal materials are hereinafter referred to, collectively, and in the alternative, as "corrosion resistant material."

Internal components such as trays or packing may be used in HPMAA light ends column 110, if desired. Such internal components, if present, may be made from the same materials as the column itself or may be constructed from one or more different materials; for example, the upper portion of the column may contain 300 series stainless steel packing, while the lower portion of the column contains HASTELLOY® B-2 packing. Trays may be used in HPMAA light ends column 110. Perforated plate trays are effective, since they have been found to be particularly resistant to MAA polymer accumulation. By the term "perforated plate trays" as used herein is meant any tray comprising a planar portion with a plurality of holes through said planar portion. Optional tray features, including but not limited to weirs, downcomers, baffles, distributors, valves, bubblecaps, and drain holes, may also be present. Examples of perforated plate trays include sieve trays, dual flow trays, and combination valve and perforation trays. It has been determined that two theoretical separation stages are desired within the HPMAA light ends column 110. If trays are used, it is preferable that two to ten perforated plate trays be used.

HPMAA light ends column 110 may be operated under a vacuum to minimize the temperature at the bottom of the column. For example, in a particular embodiment, the pressure at the bottom of the column is maintained from 40 mmHg to 80 mmHg, allowing the bottom of the column to be operated at temperatures ranging from 70° C. to 110°C.

At least one heat exchanger may be used as the heating apparatus for HPMAA light ends column 110. Desuperheated steam is an effective heat source for these exchangers. If a reboiler is used as the heat exchanger, it may be internal or external to the distillation column. Vortex breakers are also useful in the bottom of HPMAA light ends column 110.

It is oftentimes useful to add water-soluble or organic-soluble polymerization inhibitor to HPMAA light ends column 110 to inhibit polymerization of methacrylic acid. Suitable examples include but are not limited to: Hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N, N-dimethylaminophenol; 2-mercaptophenol; 4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper dimethyldithiocarbamate; copper diethyldithiocarbamate; copper dibutyldithiocarbamate; copper salicylate; methylene blue; iron; phenothiazine (PTZ); 3-oxophenothiazine; 5-oxophenothiazine; phenothiazine dimer; 1,4-benzenediamine; N-(1,4-dimethylpentyl)-N'-phenyl-1,4-benzenediamine; N-(1,3-dimethylbutyl)-N'-phenyl-1,4-benzenediamine; N-nitrosophenyl hydroxylamine and salts thereof; nitric oxide; nitrosobenzene; p-benzoquinone; or isomers thereof; mixtures of two or more thereof; mixtures of one or more of the above with molecular oxygen.

The inhibitor(s) may be used alone or combined with suitable diluents. Preferred diluents include, but are not limited to, MAA, water, and organic mixtures comprising acetone. Hydroquinone ("HQ") inhibitor is especially effective for use in HPMAA light ends column 110, and it may be added directly, or with a diluent in one or more locations throughout HPMAA light ends column 110 and its ancillaries. If used, the inhibitor may be added at a rate of 1 kg to 10 kg of HQ per 10,000 kg of HPMAA light ends column feed, for example, 1.3 kg to 8 kg of HQ per 10,000 kg of HPMAA light ends column feed. Another example would be 1.5 kg to 5 kg of HQ per 10,000 kg of HPMAA light ends column feed.

When phenolic inhibitors, such as HQ and MeHQ, are used, oxygen-containing gas may be added to the distillation column to enhance the effectiveness of the inhibitor. The term "oxygen-containing gas," as used herein, refers to any gas comprising from 0.01% up to 100% oxygen. Oxygen-containing gas may be added in one or more locations throughout HPMAA light ends column 110 and its column ancillaries. Operating temperatures and pressures impact the flammability limits and oxygen solubility within the purification system, and these properties must be taken into account when determining the appropriate oxygen concentration to be used for the oxygen-containing gas. Considerations of such factors are within the ability of one of ordinary skill in the art, and either pure oxygen or atmospheric air may be commonly employed. Surprisingly, we have found that there is an important factor affecting the efficacy of inhibition within the purification systems not previously considered with respect to oxygen addition—that is the avoidance of high oxygen concentrations within the MAA-containing stream itself. When oxygen concentrations are large relative to inhibitor concentrations, oxygen can actually increase the rate of polymerization by promoting the formation of monomer radicals. For this reason, it is not recommended that oxygen-containing gas be added to HPMAA light ends column 110 when no inhibitor is present. Further, when oxygen-containing gas and inhibitors are added to the purification system, the oxygen-containing gas may be added in a prescribed ratio relative to the inhibitor addition rate. The optimal oxygen to inhibitor ratio will vary with respect to the inhibitor used.

When HQ is the selected inhibitor, the ratio of the oxygen-containing gas feed to the HQ inhibitor feed added to the purification system may be maintained at 0.65 moles to 10 moles of $O_2$/mole of HQ, for example, at 1 mole to 8.5 moles of $O_2$/mole of HQ or at 1.5 moles to 6 moles of $O_2$/mole of HQ.

When MEHQ is the selected inhibitor, the ratio of oxygen-containing gas feed to the MEHQ inhibitor feed added to the purification system may be maintained at 1 moles to 11.5 moles of $O_2$/mole of MEHQ, for example, at 1.5 moles to 9 moles of $O_2$/mole of MEHQ, or at 2 moles to 6 moles of $O_2$/mole of MEHQ.

Light ends overhead stream 105 may be recycled for use elsewhere (e.g., in the MAA process) or may be routed to an acetone recovery vessel. To minimize condensation polymerization, vapor spaces on HPMAA light ends column 110 and its ancillaries, including condensers and interconnecting vapor lines, may be maintained at a temperature above the dew point of MAA. Insulation and electric or steam tracing are effective for this purpose.

If light ends overhead stream 105 is condensed in one or more condensers (not shown) after removal from HPMAA light ends column 110, coolant having a temperature above 16° C. may be used in the condenser to avoid freezing MAA in the stream. In a particular embodiment, tempered water in the range of 16° C. to 35° C. is used for the condenser coolant. In one embodiment, a portion of the condensate may be re-circulated through a recirculation line (not shown) back to the condenser(s) and optionally to the vapor inlet line of the condenser(s), to minimize fouling and improve condenser efficiency. The condensate may flow freely out of the re-circulation line or may be applied to the tubesheet, condenser interior surfaces, and/or inlet vapor line interior walls. If inhibitor is added to the condenser(s), it may be added into this condensate re-circulation stream to improve the distribution of the inhibitor. In another embodiment, at least a portion of this condensate recirculation stream may pass through an apparatus capable of spraying the condensate on the interior surfaces of HPMAA light ends column 110 and/or its ancillaries to wash off polymerizable condensates.

In another embodiment, an optional partial-condenser arrangement (not shown) is utilized, wherein light ends overhead stream 105 is divided into two or more streams, including at least one MAA/water stream and one water/acetone stream. In this way, the MAA/water stream can be recycled directly into an MAA process and the water/acetone stream can be routed to another process such as an acetone recovery operation, a scrubber, or a flare.

Drawn from the bottom section of the HPMAA light ends column 110 is the bottoms stream 115 that typically contains MAA and heavy ends, such as HIBA, and is generally substantially free of acetone and water. Bottoms stream 115 is fed to the second impurity removal apparatus, HPMAA heavy ends column 120. In HPMAA heavy ends column 120, the heavy impurities produced in the crude MAA production process are separated from the MAA. The heavy impurities include, but are not limited to, one or more of isobutyric acid, HIBA, mesityl oxide, MOMPA, methylmethacrylate, propionic acid, methyacrylamide, sulfates, and PTZ. HPMAA heavy ends column 120 and its column ancillaries are preferably constructed of corrosion resistant material, as described above for HPMAA light ends column 110.

Internal components such as trays or packing may be used in HPMAA heavy ends column 120, if desired. Internals, if present, may be made from the same materials as the column itself or may be constructed from one or more different materials; for example, the upper portion of HPMAA heavy ends column 120 may contain 300 series stainless steel trays, while the lower portion of the column may contain 904L trays. Trays may be used in HPMAA heavy ends column 120, for example, perforated plate trays, since they have been found to be particularly resistant to MAA polymer accumulation. It has been determined that at least five theoretical separation stages are desired within the HPMAA heavy ends column 120. If trays are used, it is preferable that five to fifteen perforated plate trays are used. It is further possible that the HPMAA heavy ends column 120 may be operated under a vacuum to minimize the bottoms temperature. For example, the pressure at the bottom of the HPMAA heavy ends column 120 should be maintained at 50 mmHg to 100 mmHg, allowing the bottom of the HPMAA heavy ends column 120 to be operated at temperatures ranging from 80° C. to 120° C.

At least one heat exchanger (not shown) may be used as the heating apparatus for HPMAA heavy ends column 120. Desuperheated steam is preferred as the heat exchanger's heat source. If a reboiler is used as the heat exchanger, it may be internal or external to the column. Vortex breakers are also useful in the bottom of HPMAA heavy ends column 120.

Heavy ends, such as HIBA and other impurities, are removed from the bottom of HPMAA heavy ends column 120 via heavy ends column bottoms stream 130. The HPMAA heavy ends column bottoms stream 130 may be disposed of, but optionally some components of this stream may be recovered and used as a fuel. Optionally, bottoms stream 130 may be further processed in an independent stripping system (not shown) to recover residual MAA. In one embodiment of an independent stripping system (not shown), bottoms stream 130 may be heated in one or more glass-lined stripping vessels with live steam (steam that comes into direct contact with the MAA-containing heavies column bottoms stream). The stripping vessels may be operated at sub-atmospheric pressure to maximize the recovery of MAA. The recovered MAA may be recycled back, for example, into a MAA process or into a methacrylic acid-ester process. In one embodiment, the heavies column bottoms are further processed in a spent sulfuric acid unit, either alone or in combination with spent acid streams selected from the list including ACH-based MAA process acid residues, ACH-based MMA process acid residues, and acrylic ester process acid residues, to recover sulfur.

To minimize condensation polymerization, vapor spaces on HPMAA heavy ends column 120 and its ancillaries, including condensers and interconnecting vapor lines, may be maintained at a temperature above the dew point of MAA. Insulation and electric or steam tracing are effective for this purpose.

The HPMAA heavy ends column overhead stream 125 contains a significant amount of MAA as well as water, acetone, and other light ends. Overhead stream 125 may be at least partially condensed in one or more condensers (not shown) to remove at least a portion of the light ends. If overhead stream 125 is so condensed, tempered water may be used in the condenser(s) to avoid freezing the MAA in the stream. To maintain the required purity of the product stream 135, it is often necessary to return a portion of the condensate back to HPMAA heavy ends column 120 via heavy ends reflux stream 155. The fraction of condensate returned may vary from 0% to 100%, depending on the operating conditions of HPMAA heavy ends column 120 and the MAA purity level desired in the product stream 135. In a particular embodiment, a portion of the condensate may be re-circulated back to the condenser(s) and optionally to the condenser inlet line, to minimize fouling and improve condenser efficiency. The condensate may flow freely out of the re-circulation line or may be applied to the tubesheet, condenser interior surfaces, and/or inlet vapor line interior walls. If inhibitor is added to the condenser(s), it may be added into this condensate re-circulation stream to improve the distribution of the inhibitor. In another embodiment, at least a portion of this condensate re-circulation stream may pass through an apparatus capable of spraying the condensate on the interior surfaces of HPMAA heavy ends column 120 and/or its ancillaries to wash off polymerizable condensates. The remaining condensate, comprising MAA and light end impurities, is then returned to HPMAA light ends column 110 as heavy ends column recycle stream 165.

Removal of the product stream 135 from the side of the second distillation column of the process, i.e., from the HPMAA heavy ends column 120 as shown in FIG. 1, instead of from the top of the column 120, allows for improved operation of HPMAA heavy ends column 120 and for the production of a higher purity of HPMAA. This configuration is referred to herein as a "side-draw" configuration. Increased purity of HPMAA can be achieved by using a side draw configuration due to the tray composition in the middle section of the HPMAA heavy ends column 120 being lower in light ends impurities than the trays at the top of the column.

Additionally, because the highest temperature occurs at the bottom of HPMAA heavy ends column 120, polymers or other undesirable insoluble impurities that may form are less likely to be present in a side-draw stream versus HPMAA product drawn directly from the bottom of the column. While optional filtration of product stream 135 through means known in the art may be used, the use of the side-draw configuration in this embodiment may reduce the level of potential insoluble impurities in the HPMAA product stream. Thus, the need for filtration may be minimized or possibly eliminated and the cost of operation reduced. It is noted that the side-draw configuration may instead be applied to the second distillation column of a two-column purification system, in accordance with the present invention, even where the second column is not the heavy ends column, but is a light ends column. This will be clarified hereinafter in connection with the description of the embodiment shown in FIG. 3.

Figure 2:
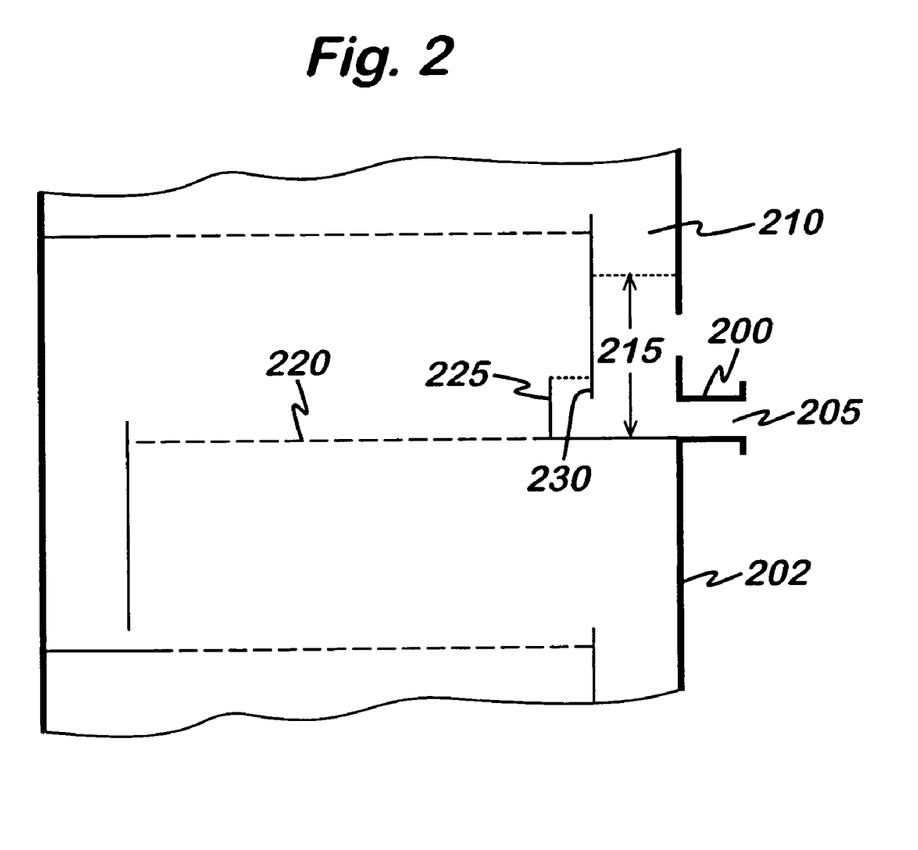
FIG. 2 is a schematic diagram of one embodiment of a side draw configuration useful in connection with the process for producing HPMAA of the present invention.

FIG. 2 is a schematic sectional diagram representing one embodiment of a side draw configuration adapted for use with heavy ends removal column 120 of FIG. 1. This side draw configuration may be used with perforated plate distillation trays, such as sieve trays, but is also suitable for use with trays of other types as well. As shown in FIG. 2, a piping connection 200 is made with the sidewall of the distillation column 202. With regard to the embodiment of FIG. 1, the distillation column 202 of FIG. 2 is analogous to the heavy ends removal column 120. The piping connection shown in FIG. 2 allows liquid accumulation in downcomer 210 to be drawn through opening 205. Inlet weir 225 restricts flow out of downcomer 210 onto side draw tray 220, thereby maintaining sufficient liquid head in downcomer 210 to create liquid outflow via opening 205. This liquid outflow is side draw product stream 135. The appropriate height of weir 225 is dependent on a number of variables including: the height 215 of liquid within downcomer 210 (also known as "downcomer backup"), the pressure above side draw tray 220, the downcomer clearance 230, the desired flow rate of side draw product stream 135, and the diameter of opening 205. Selection of an appropriate height for inlet weir 225 is within the ability of one of ordinary skill in the art of distillation design. In one possible arrangement, for example, the height 215 of liquid within downcomer 210 is 11 inches (27.94 cm), the pressure above side draw tray 220 is 45 mmHg, downcomer clearance 230 is ¾-inch (1.91 cm), the desired flow rate of side draw product stream 135 is approximately 11,000 kg/hr, the diameter of opening 205 is 3 inches (7.62 cm), and the height of weir 225 is 6 inches (15.24 cm).

It is oftentimes useful to add one or more inhibitors, such as those listed above, to HPMAA heavy ends column 120 with or without a diluent. Inhibitor may be added in one or more locations throughout HPMAA heavy ends column 120 and its ancillaries.

If HQ inhibitor is used, the inhibitor may be added (optionally with a diluent) at a rate of 1 kg to 10 kg of HQ per 10,000 kg of HPMAA heavy ends column 120 feed, for example, 1.3 kg to 8 kg of HQ per 10,000 kg of HPMAA heavy ends column 120 feed or 1.5 kg to 5 kg of HQ per 10,000 kg of HPMAA heavy ends column 120 feed.

MEHQ is a particularly effective inhibitor and may be added directly, or with a diluent such as MAA, in one or more locations throughout HPMAA heavy ends column 120 and its ancillaries. If used, MEHQ may be added at a rate of 1 kg to 15 kg of MEHQ per 10,000 kg of HPMAA heavy ends column feed stream 115, for example, 1.5 kg to 12 kg of MEHQ per 10,000 kg of HPMAA heavy ends column feed, or 2 kg to 9 kg of MEHQ per 10,000 kg of HPMAA heavy ends column feed.

As described above, when phenolic inhibitors, such as HQ and MEHQ, are used, oxygen-containing gas may be added to the distillation column to enhance the effectiveness of the inhibitor. Oxygen-containing gas may be added in one or more locations throughout HPMAA heavy ends column 120 and its column ancillaries. Operating conditions and concerns and recommended oxygen-to-inhibitor ratios for HPMAA heavy ends column 120 are identical to those described in connection with HPMAA light ends column 110.

Side-draw removal of the HPMAA product stream increases the number of inhibitor options for use in HPMAA heavy ends column 120. This is due to the fact that inhibitors are generally heavy components that exit distillation column 120 through the bottoms stream. Thus, in an embodiment wherein the product stream is drawn from the bottom of column 120, any added inhibitor would exit along with it. By way of contrast, when the product is drawn from the side of the column as shown in FIG. 1, all of the inhibitor is not drawn off with the product. Thus, in the embodiment illustrated in FIG. 1, a wide variety of inhibitors may be supplied directly to the HPMAA heavy ends column 120 itself and may even include inhibitors that are undesired in the product HPMAA, provided they are added to the column at locations below the point where the side draw stream is removed.

Accordingly, in some embodiments, PTZ may be added directly to the lower section of HPMAA heavy ends column 120 to minimize polymer formation in the bottoms of the column. If used, PTZ may be added (optionally with a diluent) at a rate of 0.005 kg to 8 kg of PTZ per 10,000 kg of HPMAA heavy ends column 120 feed, for example, 0.01 kg to 5 kg of PTZ per 10,000 kg of HPMAA heavy ends column 120 feed, or 0.05 kg to 1 kg of PTZ per 10,000 kg of HPMAA heavy ends column 120 feed.

HPMAA product stream 135 may be cooled before storage to inhibit polymerization. As with all polymerizable monomers, it is beneficial for the product methacrylic acid to comprise polymerization inhibitors in order to prevent polymerization in shipment and storage. Any of the inhibitors previously listed as suitable for use in the distillation columns may be employed for this purpose. However, when MAA is used in specialty polymer production, MeHQ is most commonly utilized as the inhibitor, and is typically employed at a concentration of between 200 ppm and 300 ppm. In some embodiments of the present invention, a variable amount of MeHQ inhibitor may be added directly to the HPMAA product stream 135 to ensure that the HPMAA product stream inhibitor concentration remains within final product specifications.

Often, methacrylic acid may not have to be freed of MeHQ inhibitor prior to use by polymer manufacturers in polymerization reactions. This applies particularly to the preparation of copolymers where MAA is less than 50 wt % of the monomer mixture, based on the total weight of the mixture. In such instances, somewhat larger quantities of initiator may be employed than with uninhibited monomer. Alternatively, because MeHQ is a phenolic inhibitor, some specialty MAA polymer manufacturers may instead choose to perform their polymerization reactions in the absence of oxygen, thereby rendering the MeHQ substantially inactive in the reaction system. If, however, it is not practical to adjust initiator levels or exclude oxygen from the reaction system, known methods such as alkaline wash, treatment with a suitable ion-exchange resins, or distillation of the methacrylic acid product may be employed to remove the MeHQ inhibitor prior to use.

Examples of the HPMAA product stream produced by the present invention include a composition wherein the assay of the MAA is at least 99 wt %, water is present at a concentration of up to 500 ppm (0.05 wt % H2O), the methacrolein content of the MAA is up to 1000 ppm (0.1 wt % methacrolein), and the HIBA content of the MAA is up to 9,000 ppm (0.9 wt % HIBA), all weight percents being based upon the total weight of the HPMAA product stream.

Another example of the HPMAA product stream of the present invention includes a composition wherein the assay of the HPMAA is at least 99 wt %, water is present at a concentration of up to 300 ppm (0.03 wt % H2O), the methacrolein content of the HPMAA is up to 500 ppm (0.05 wt % methacrolein), and the HIBA content of the HPMAA is up to 5,000 ppm (0.5 wt % HIBA), all weight percents being based upon the total weight of the HPMAA product stream.

Yet another example of the HPMAA product stream of the present invention includes a composition wherein the assay of the HPMAA is at least 99 wt %, water is present at a concentration of up to 200 ppm (0.02 wt % H2O), the methacrolein content of the HPMAA is up to 200 ppm (0.02 wt % methacrolein), and the HIBA content of the HPMAA is up to 1,500 ppm (0.15 wt % HIBA), all weight percents being based upon the total weight of the HPMAA product stream.

An additional example of a product HPMAA stream produced by the present invention includes a composition wherein the assay of the HPMAA is at least 99 wt %, water is present at a concentration of up to 150 ppm (0.015 wt % H2O), the methacrolein content of the HPMAA is up to 50 ppm (0.005 wt % methacrolein), and the HIBA content of the HPMAA is up to 1,000 ppm (0.10 wt % HIBA), all weight percents being based upon the total weight of the HPMAA product stream.

An example of the HPMAA product stream produced by the present invention further includes a composition wherein the collective MOMPA and MMA content of the HPMAA is up to 1000 ppm (0.1 wt % of both MOMPA and MMA), and the methacrylamide content of the HPMAA is up to 750 ppm (0.075 wt % MAM), all weight percents being based upon the total weight of the HPMAA product stream.

Another example of the HPMAA product stream of the present invention further includes a composition wherein the collective MOMPA and MMA content of the HPMAA is up to 500 ppm (0.05 wt % of both MOMPA and MMA), and the methacrylamide content of the HPMAA is up to 500 ppm (0.05 wt % MAM), all weight percents being based upon the total weight of the HPMAA product stream.

Yet another example of the HPMAA product stream of the present invention further includes a composition wherein the collective MOMPA and MMA content of the HPMAA is up to 200 ppm (0.02 wt % of both MOMPA and MMA), and the methacrylamide content of the HPMAA is up to 100 ppm (0.01 wt % MAM), all weight percents being based upon the total weight of the HPMAA product stream.

A yet additional example of a product HPMAA stream produced by the present invention further includes a composition wherein the collective MOMPA and MMA content of the HPMAA is up to 100 ppm (0.01 wt % of both MOMPA and MMA), and the methacrylamide content of the HPMAA is up to 25 ppm (0.0025 wt % MAM), all weight percents being based upon the total weight of the HPMAA product stream.

An example of the HPMAA product stream produced by the present invention further includes a composition wherein the acetic acid content of the HPMAA product stream is up to 1000 ppm (0.1 wt % acetic acid), the acetone content is up to 800 ppm (0.08 wt % acetone), the acrylic acid content is up to 400 ppm (0.04 wt % acrylic acid), and the propionic acid content is up to 200 ppm (0.02 wt % propionic acid), all weight percents being based upon the total weight of the HPMAA product stream.

Another example of the HPMAA product stream of the present invention further includes a composition wherein the acetic acid content of the HPMAA product stream is up to 750 ppm (0.075 wt % acetic acid), the acetone content is up to 400 ppm (0.04 wt % acetone), the acrylic acid content is up to 200 ppm (0.02 wt % acrylic acid), and the propionic acid content is up to 150 ppm (0.015 wt % propionic acid), all weight percents being based upon the total weight of the HPMAA product stream.

Yet another example of the HPMAA product stream of the present invention further includes a composition wherein the acetic acid content of the HPMAA product stream is up to 200 ppm (0.02 wt % acetic acid), the acetone content is up to 50 ppm (0.005 wt % acetone), the acrylic acid content is up to 25 ppm (0.0025 wt % acrylic acid), and the propionic acid is up to 100 ppm (0.01 wt % propionic acid), all weight percents being based upon the total weight of the HPMAA product stream.

An additional example of a product HPMAA stream produced by the present invention further includes a composition wherein the acetic acid content of the HPMAA product stream is up to 100 ppm (0.01 wt % acetic acid), the acetone content is up to 25 ppm (0.0025 wt % acetone), the acrylic acid content is up to 10 ppm (0.001 wt % acrylic acid), and the propionic acid content is up to 50 ppm (0.005 wt % propionic acid), all weight percents being based upon the total weight of the HPMAA product stream.

Figure 3:
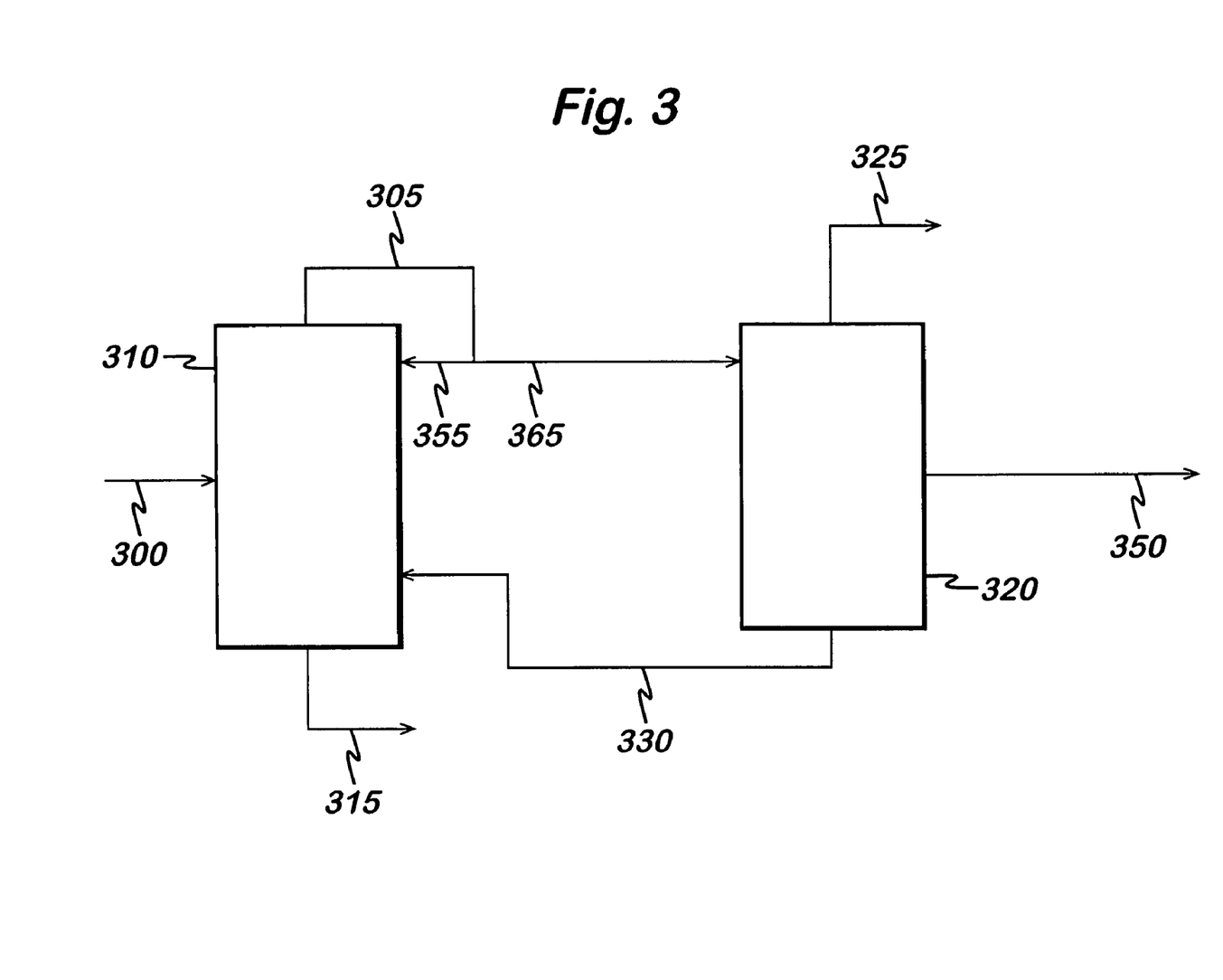
FIG. 3 is a schematic flow diagram of an alternative embodiment of the process for producing HPMAA in accordance with the present invention.

Another embodiment of an improved HPMAA purification system is shown in FIG. 3. This embodiment utilizes a "reverse-order" configuration to purify crude MAA stream 300 into an HPMAA product stream in accordance with the present invention. Crude MAA stream 300 is initially fed to the first impurity removal apparatus, HPMAA heavies column 310. In HPMAA heavies column 310, heavy ends, including HIBA, are removed from the bottom of the column via line 315. As will be recognized by persons of ordinary skill in the art, early removal of heavies in this embodiment minimizes HIBA decomposition to water and light ends in the next column.

HPMAA heavies column 310 and its column ancillaries are preferably constructed of corrosion resistant material, as previously described for HPMAA light ends column 110. Internal components such as trays or packing may be used in HPMAA heavies column 310, if desired. Internals, if present, may be made from the same materials as the column itself or may be constructed from one or more different materials. Trays may be used in HPMAA heavies column 310, for example, perforated plate trays, since they have been found to be particularly resistant to MAA polymer accumulation. It has been determined that at least five theoretical separation stages are desired within the HPMAA heavies column 310. If trays are used, it is preferable that five to fifteen perforated plate trays are used. HPMAA heavies column 310 may be operated under a vacuum to minimize the temperature of the bottom of the column. For example, in a particular embodiment, the pressure at the bottom of the HPMAA heavies column 310 is maintained at 50 mmHg to 90 mmhg, allowing the bottom of the HPMAA heavies column 310 to be operated at 85° C. to 125° C. At least one heat exchanger (not shown) may be used as the heating apparatus for HPMAA heavies column 310. Desuperheated steam may be used effectively as the heat exchanger's heat source. If a reboiler is used as the heat exchanger, it may be internal or external to the column. Vortex breakers are also useful in the bottom of HPMAA heavies column 310.

While some inhibitors may still be present in the crude MAA from prior processing, it is oftentimes useful to add inhibitors such as those listed above, with or without diluents, to HPMAA heavies column 310. HQ inhibitor is especially effective and may be added directly, or with a diluent such as water, in one or more locations throughout HPMAA heavies column 310 and its ancillaries. If used, the inhibitor may be added at a rate of 1 kg to 10 kg of HQ per 10,000 kg of feed to the HPMAA heavies column 310, for example, at a rate of 1.3 kg to 8 kg of HQ per 10,000 kg of feed to the HPMAA heavies column 310, or 1.5 kg to 5 kg of HQ per 10,000 kg of feed to the HPMAA heavies column 310.

As described above, when phenolic inhibitors, such as HQ and MEHQ, are used, oxygen-containing gas may be added to the distillation column to enhance the effectiveness of the inhibitor. Oxygen-containing gas may be added in one or more locations throughout HPMAA heavies column 310 and its column ancillaries. Operating conditions and concerns and recommended oxygen-to-inhibitor ratios for HPMAA heavies column 310 are substantially identical to those described in connection with HPMAA light ends column 110.

HIBA, and other heavy ends impurities are removed from the bottom of the HPMAA heavies column 310 via stream 315 and it may be disposed of or recovered for use as fuel. Optionally, the heavies column bottoms can be further processed in an independent stripping system (not shown) to recover residual MAA. In one embodiment of an independent stripping system (not shown), the heavies column bottoms are heated in one or more glass-lined stripping vessels with live steam. The stripping vessels may be operated at sub-atmospheric pressure to maximize the recovery of MAA. In one embodiment, the heavies column bottoms are further processed in a spent sulfuric acid unit, either alone or in combination with spent acid streams selected from the list including ACH-based MAA process acid residues, ACH-based MMA process acid residues, and acrylic ester process acid residues, to recover sulfur.

The HPMAA heavies column overhead stream 305 contains a significant amount of MAA as well as water, acetone, other light ends, and trace amounts of heavy ends. HPMAA heavies column overhead stream 305 may be at least partially condensed in one or more condensers (not shown). Further, the condensed stream may be split into a reflux stream 355 and a feed stream 365.

To maintain the required purity of lights column feed stream 365, it is often necessary to return a portion of the condensate back to the heavies column 310 via reflux stream 355; the fraction of condensate returned may vary from 0% to 100%, depending on the operating conditions of HPMAA heavies column 310 and the purity level desired for feed stream 365. The remaining condensate is then transferred via feed stream 365 to HPMAA lights column 320. Tempered water may be used in the heavies column condenser(s) (not shown) to avoid freezing MAA in the stream. To minimize condensation polymerization, vapor spaces on HPMAA heavies column 310, and its ancillaries including condensers and interconnecting vapor lines, may be maintained at a temperature above the dewpoint of MAA. Insulation and electric or steam tracing are effective for this purpose.

In a particular embodiment, a portion of the condensate may be recirculated back to the condenser (not shown), and optionally to the condenser inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser, it may be added to this condensate recirculation stream to improve the distribution of the inhibitor. In a particular embodiment, at least a portion of this condensate recirculation stream may pass through an apparatus capable of spraying the condensate on the interior surfaces of HPMAA heavies column 310 and/ or its ancillaries to wash off polymerizable condensates.

HPMAA lights column 320 removes water, acetone, and other light impurities, where present, from the MAA via stream 325. A partial-condenser arrangement (not shown) may be used, wherein stream 325 is at least partially condensed into a liquid. If stream 325 is so condensed, tempered water may be used as a coolant to avoid freezing MAA in the stream 325. To minimize condensation polymerization, vapor spaces on HPMAA lights column 320, and its ancillaries including condensers and interconnecting vapor lines, may be maintained at a temperature above the dewpoint of MAA Insulation and electric or steam tracing are effective for this purpose. In a particular embodiment, a portion of the condensate may be recirculated back to the condenser and optionally to the condenser inlet line, to minimize fouling and improve condenser efficiency. The condensate may flow freely out of the recirculation line or may be applied to the tubesheet, condenser interior surfaces, and/or inlet vapor line interior walls. If inhibitor is added to the condenser, it may be added to this condensate recirculation stream to improve the distribution of the inhibitor. In an particular embodiment, at least a portion of this condensate recirculation stream may pass through an apparatus capable of spraying the condensate on the interior surfaces of HPMAA lights column 320 and/or its ancillaries to wash off polymerizable condensates.

HPMAA lights column 320 and its column ancillaries are preferably constructed of corrosion resistant material, as previously described for HPMAA lights column 110. Internal components such as trays or packing may be used in HPMAA lights column 320, if desired. Internals, if present, may be made from the same materials as the column itself or may be constructed from one or more different materials. Perforated plate trays are especially effective, since they have been found to be particularly resistant to MAA polymer accumulation. It has been determined that at least two theoretical separation stages are desired within the HPMAA lights column 320. If trays are used, it is preferable that two to ten perforated plate trays are used. HPMAA lights column 320 may be operated under a vacuum (i.e., below atmospheric pressure) to minimize bottoms temperature. In a particular embodiment, the pressure at the bottom of HPMAA lights column 320 is maintained at 60 mmHg to 100 mmHg, allowing the bottom of HPMAA lights column 320 to be operated at 75° C. to 115° C.

At least one heat exchanger (not shown) may be used as the heating apparatus for the HPMAA lights column 320. Desuperheated steam is effective as the heat exchanger's heat source. If a reboiler is used as the heat exchanger, it may be internal or external to the column. Vortex breakers are also useful in the bottom of HPMAA lights column 320.

HPMAA product stream 350 exits HPMAA lights column 320 from the side of the column 320 having purity levels greater than or equal to 99% and containing less than 0.05% water. Suitable connecting means, such as those previously described and depicted in FIG. 2, are used to connect the piping of stream 350 to the side of column 320. Similar to the side draw of the Heavy Ends Removal Column 120, details of the side draw of the HPMAA Lights Column 320 of FIG. 3 are illustrated in FIG. 2. With respect to the reverse order process of FIG. 3, the distillation column 202 represented in FIG. 2 is the HPMAA Lights Column 320. Likewise the stream exiting the opening 205 is the product stream 350. Product stream 350 may be cooled before storage to inhibit polymerization.

While optional filtration of product stream 350 may be used as described in the previous embodiment depicted in FIG. 1, the use of the side-draw configuration in this embodiment may reduce the level of potential impurities in the HPMAA product stream. Thus, the need for filtration may be minimized and the cost of operation reduced.

As shown in FIG. 3, heavy end impurities, which may accumulate in the bottom of HPMAA lights column 320, are removed via stream 330 and recycled back to HPMAA heavies column 310. This recycle step allows the MAA present in stream 330 to be recovered in column 310. Any heavy ends and undesirable impurities present in stream 330 will exit HPMAA heavies column 310 with the other heavy end components in stream 315.

It is oftentimes useful to add inhibitors, such as those listed above, to HPMAA lights column 320, optionally with a diluent. Inhibitor may be added in one or more locations throughout HPMAA lights column 320 and its ancillaries.

The side-draw removal of the HPMAA product stream 350 increases the number of inhibitor options for use in HPMAA lights column 320. This is due to the fact that inhibitors are generally heavy components that exit a distillation column through its bottoms. Thus, when the product stream is drawn from the bottom of the column any inhibitor added to the column exits along with it. By way of contrast, when the product is drawn from the side of the column, any inhibitor added to the column below the product removal point—e.g., below the side-draw tray—is not drawn off with the product; rather, the inhibitor drops to the bottom of the column for removal. Thus, in the reverse-order embodiment illustrated in FIG. 3, a wide variety of inhibitors may be employed in HPMAA lights column 320 and different inhibitors may be added at different locations in the HPMAA lights column 320, if desired.

PTZ is particularly useful for minimizing polymer formation in the bottoms of HPMAA Lights Column 320. If used, PTZ may be added (optionally with a diluent) at a point on the HPMAA Lights Column 320 below the side-draw tray and at a rate of 0.005 kg to 8 kg of PTZ per 10,000 kg of HPMAA lights column 320 feed, for example, 0.01 kg to 5 kg of PTZ per 10,000 kg of HPMAA lights column 320 feed, or 0.05 kg to 1 kg of PTZ per 10,000 kg of HPMAA lights column 320 feed.

If HQ inhibitor is used, it may be added (optionally with a diluent) at a rate of 1 kg to 10 kg of HQ per 10,000 kg of HPMAA lights column 320 feed, for example, 1.3 kg to 8 kg of HQ per 10,000 kg of HPMAA lights column 320 feed, or 1.5 kg to 5 kg of HQ per 10,000 kg of HPMAA lights column 320 feed.

MEHQ inhibitor may also be added to HPMAA lights column 320 in this embodiment and may be added directly, or with a diluent such as MAA, throughout HPMAA lights column 320 and its ancillaries. In general, satisfactory performance will be achieved in HPMAA lights column 320 if the MEHQ addition rates for HPMAA Heavy Ends column 120, as described above, are utilized. Optionally, a variable amount of MEHQ inhibitor may be added directly to the HPMAA product stream 350 to ensure that the HPMAA product stream inhibitor concentration is within final product specifications.

As described above, when phenolic inhibitors, such as HQ and MEHQ, are used, oxygen-containing gas may be added to the distillation column to enhance the effectiveness of the inhibitor. Oxygen-containing gas may be added in one or more locations throughout HPMAA lights column 320 and its column ancillaries. Operating conditions and concerns and recommended oxygen-to-inhibitor ratios for HPMAA lights column 320 are substantially identical to those described in connection with HPMAA lights column 110.

In addition to the aforementioned difficulties of producing specialty MAA polymers from methacrylic acid product comprising significant amounts of HIBA, it should be noted that the presence of HIBA in crude methacrylic acid could also have detrimental effects in purification processes, including the purification process of the present invention as well as others. Specifically, HIBA that is present in crude methacrylic acid may thermally decompose during purification to produce decomposition products including acetone, carbon monoxide, and water. Such in-situ decomposition-product formation is counterproductive to the objective of water and acetone removal and may in some cases prevent the attainment of desired low-impurity levels of the product MAA.

It has been determined that decomposition of HIBA during purification is promoted by acid-catalysts, such as sulfuric acid. One or more of such acid-catalysts may be present in the crude methacrylic acid as a result of prior processing. For example, crude methacrylic acid derived from an ACH-process may contain residual sulfuric acid or other compounds capable of providing sulfate ($SO_4^{-2}$) ions.

The extent of HIBA decomposition is dependent on several process variables including acid-catalyst concentration in the bottom of the column, column bottoms temperature, and bottoms residence time. By controlling one or more of these variables the extent of HIBA decomposition during purification may be minimized, thereby improving operation of the purification process by reducing the water load on the purification system.

By operating MAA purification distillation columns at less than atmospheric pressure (as measured in the vapor space below Tray 1), it is possible to maintain the column bottoms temperatures at less than 150° C. For minimization of HIBA decomposition in an MAA purification column, the temperature at the bottom of column may be maintained at not more than 145° C., for example not more than 120° C. or not more than 100° C. The temperature at the bottom of the column may even be maintained at not more than 90° C.

Maintaining low bottoms residence time in MAA purification columns also serves to minimize HIBA decomposition. As used herein, the term "bottoms residence time" refers to the average time a given unit-volume of material remains within the bottom sump of the column and its ancillaries (including but not limited to the reboiler and the interconnecting circulation piping between the sump and the reboiler). Generally, the bottoms residence time can be determined by calculating, at steady state operating conditions, the total process fluid volume in the bottom (sump) of the column, the reboiler, and associated bottoms piping, and then dividing this total process fluid volume by the volumetric flow rate (removal rate) of the bottoms stream. While the maximum residence time is ultimately determined by the physical dimensions of the purification equipment (distillation column diameter and the like), the actual bottoms residence time employed may be further controlled through the adjustment of process operating variables such as the sump operating level, boil-up rate, column feed rate, and column bottoms removal rate. It has been determined that HIBA decomposition may be minimized when bottoms residence time is maintained at not more than 48 hours, for example not more than 24 hours, or not more than 15 hours, or even not more than 5 hours.

The decomposition of HIBA in purification may also be minimized by maintaining the total acid-catalyst concentration in the bottom of a distillation column (as measured in the bottoms stream) at not more than 2.5 wt % (25,000 ppm), for example not more than 1.5 wt % (15,000 ppm), or not more than 0.5 wt % (5,000 ppm), based on the total weight of the bottoms stream. This may be achieved by maintaining low acid-catalyst concentration in the crude MAA feed to purification, or by controlling bottoms composition through the adjustment of column operating variables such as MAA vaporization rate and bottoms residence time. Optional treatment methods, such as treatment with stabilizing agents (described below), may also be employed to neutralize at least a portion of the acid-catalyst and thereby lower the acid-catalyst concentration.

In addition to the methods described above, the problem of thermal decomposition of HIBA may be avoided, at least in part, by minimizing the HIBA content in the crude methacrylic acid prior to purification. In the case of crude methacrylic acid derived from ACH-processes, the formation of HIBA, and thus the resulting final HIBA content in crude methacrylic acid, may be minimized through optimization of various crude MAA production steps. For example, by utilizing essentially anhydrous conditions in the hydrolysis process-step, HIBA formation can be minimized. Such anhydrous conditions may be achieved through the use of dry acetone cyanohydrin, dry sulfuric acid (e.g., oleum), and SO3 addition, either alone or in combination, in the hydrolysis step of the MAA production process to minimize HIBA formation. Additionally, the use of high temperatures, long residence times, and plug-flow conditions, either alone or in combination, will improve conversion of HIBA to MAM during the thermal conversion (aka: "cracking") step of the MAA production process.

It will be obvious to one of ordinary skill in the art that the HIBA content of crude methacrylic acid may also be minimized through the use of processes that do not form MAA via the HIBA intermediate. For example, C-4 based methacrylic acid processes typically utilize methacrolein as an intermediate and can therefore be reasonably expected to not contain a significant level of HIBA impurity in the resultant crude MAA product. Purification of such 'low-HIBA' crude methacrylic acid streams in the above-described distillation process to obtain low-HIBA content methacrylic acid is within the scope of the present invention.

In addition to minimizing the HIBA content in the crude methacrylic acid prior to purification, optional HIBA treatment methods may also be employed during the purification process, for example, in combination with the distillation method of the present invention, to further improve the quality and reduce the impurity levels of product methacrylic acid. These HIBA treatment methods include stabilization of HIBA to prevent thermal decomposition during purification and elimination of HIBA prior to purification.

Such optional treatment methods may be used alone or in combination with the above-described crude MAA production steps to minimize HIBA content in the crude MAA product. By employing these optional HIBA treatment methods, the quality of said optionally treated product methacrylic acid could be further improved.

As previously stated, it has been discovered that the thermal decomposition reaction of HIBA is catalyzed by the presence of acid-catalyst, such as sulfuric acid. By neutralizing at least a portion of these acid-catalysts prior to purification of the crude methacrylic acid stream, decomposition of HIBA may be substantially avoided.

In one embodiment of this HIBA treatment method, treatment of the crude methacrylic acid with stabilizing agents, such as for example, magnesium oxide, magnesium hydroxide, sodium hydroxide, or ammonia, serves to neutralize the acid-catalyst. Salts formed by neutralization of the acid-catalyst are then removed from the treated methacrylic acid through known filtration methods, thereby stabilizing the HIBA and allowing thermal decomposition to be substantially avoided.

In a particular embodiment, wherein sulfuric acid is the acid-catalyst present in the crude MAA, magnesium oxide is used as the stabilizing agent However, in this embodiment, the substantially insoluble magnesium sulfate salts resulting from the neutralization are not filtered from the crude methacrylic acid following treatment. The treated crude methacrylic acid is then purified in the distillation process of the present invention. The heavy ends stream from the distillation process comprises magnesium sulfate (MgSO4) and is further processed in a spent acid recovery unit (not shown). The presence of magnesium sulfate in the spent acid recovery unit is beneficial in the prevention of corrosion of the process apparatus.

In an alternative embodiment, the crude methacrylic acid stream is contacted with a suitable ion exchange resin (IER) to remove the acid-catalyst, for example a suitable IER having a basic functionality. Contact may be achieved by passing the crude MAA stream through an IER bed or by adding IER directly into the crude MAA stream, followed by filtration after treatment is complete. Suitable IER's having basic functionality include, but are not limited to, one or more selected from the list including AMBERLYST® A-21 or AMBERLYST® A-26 (both available from Rohm and Haas Company of Philadelphia, Pa.). Using these methods, HIBA is stabilized and the decomposition of HIBA is substantially avoided in purification.

In comparison to the stabilization of HIBA, the destruction of HIBA prior to purification is a HIBA treatment method that minimizes thermal decomposition of HIBA in the purification process and reduces the concentration of HIBA in the crude MAA stream. The HIBA destruction treatment method comprises contacting the crude MAA stream with one or more Lewis acid components that are, for example, strong Lewis acids. The Lewis acid components can include sulfuric acid, phosphoric acid, "superacid" (e.g., TiOSO4-H2SO4 or ZrOSO4-H2SO4), an ion exchange resin with acidic functionality (such as, but not limited to, AMBERLYST® 15 available from Rohm and Haas Company of Philadelphia, Pa.), and combinations thereof. After the addition of the Lewis acids the mixture is then heated, for example above 90° C., to substantially decompose the HIBA to water, acetone, and carbon monoxide prior to final purification. Such HIBA decomposition products are removed as light ends in the purification process of the present invention described hereinabove, resulting in an MAA product with low levels of water and HIBA impurities.

In one embodiment of HIBA reduction, methacrylic acid comprising HIBA is combined with 20% H2SO4, heated to at least 100° C., and optionally mixed. The heating of this mixture may be conducted at atmospheric pressure. The HIBA is substantially decomposed and the resulting light ends are then removed by distillation according to the purification method of the present invention.

It will be apparent to one of ordinary skill in the art, with the benefit of the disclosure of the present invention, that these optional HIBA treatment methods may also be employed alone, or in combination with other methacrylic acid purification processes to produce a variety of MAA products, including glacial methacrylic acid, HPMAA, and HPMAA with low HIBA content. These optional HIBA treatment methods may also be successfully applied to other methacrylic acid purification processes including, but not limited to, the three-column distillation process described in co-pending U.S. application U.S. Ser. No. 10/420,273 filed Apr. 22, 2003, the solvent extraction process described in U.S. Pat. No. 3,414,485, as well as crystallization processes and hybrid distillation/crystallization purification processes.

EXAMPLE 1

A two column side-draw purification apparatus of the type shown in FIG. 1 and FIG. 2 was used to produce HPMAA in accordance with the purification process of the present invention. In this example, lights ends column 110 comprised five sieve trays and heavy ends column 120 comprised ten sieve trays. The position of each tray within each column is hereinafter referenced by a numerical reference, with the bottom-most tray, for example, being referred to as "Tray 1". The sieve trays in light ends column 110 have ½" (1.27 cm) diameter holes and a 13% open area. All light ends column trays are installed with a 33-inch (83.82 cm) spacing between them. The sieve trays in heavy ends column 120 have ½" (1.27 cm) diameter holes and a 10.2% open area. Trays in the heavy ends column 120 are installed with variable spacing between them: Trays 1 through 4 are installed 24 inches (60.96 cm) apart from one another, Tray 5 is 36 inches (91.44 cm) above Tray 4, and Trays 5 through 10 are installed 33 inches (83.82 cm) apart from one another. Heavy ends column Tray 7 is a sidedraw tray, of the type illustrated in FIG. 2 and described in detail hereinabove. In this example, both columns were operated at less than atmospheric pressure. Approximately 7,250 kg/hr of crude MAA feed stream 100 was supplied to light ends column 110. Crude MAA feed stream 100 was derived from an ACH-process and comprised 95.05 wt % MAA, 2.00 wt % water, 0.8 wt % HIBA, 0.25 wt % methacrylamide, 0.90 wt % acetone, and 1.00 wt % MOMPA, based on the total weight of the crude MAA stream. The crude MAA stream was co-fed with heavy ends column recycle stream 165 to Tray 5 (top) of light ends column 110. Aqueous HQ inhibitor was provided to light ends column 110; atmospheric air was also supplied to the bottom section of the column 110 at a rate sufficient to ensure the efficacy of the HQ inhibitor. Sufficient steam was supplied to the light ends column reboiler (not shown) to maintain a bottoms temperature of 90° C. at 58 mmHg bottoms pressure. Approximately 900 kg/hr of light ends stream 105, comprising water and acetone, was removed from light ends column 110. Light ends bottoms stream 115, comprising greater than 98 wt % MAA and not more than 1.0 wt % H2SO4, based on the total weight of the light ends bottoms stream, was withdrawn from light ends column 110 and fed to the sump area (below Tray 1) of heavy ends column 120.

A solution of MeHQ inhibitor in MAA was provided to heavy ends column 120. Atmospheric air was also supplied to the bottom section of the heavy ends column 120 at a rate sufficient to ensure the efficacy of the MeHQ inhibitor. Sufficient steam was supplied to the heavy ends column reboiler (not shown) to maintain a bottoms temperature of 100° C. at 75 mmHg bottoms pressure in the heavy ends column 120. Overhead stream 125 was withdrawn from the upper section of heavy ends column 120, condensed, and partially refluxed. Approximately 2,800 kg/hr of MAA-containing heavy ends column recycle stream 165 was returned to light ends column 110. Approximately 1,550 kg/hr of bottoms stream 130, comprising MOMPA, MAM, and HIBA, was removed from heavy ends column 120. The bottom of the heavy ends column 120 had an internal diameter of 2.1 m and provided a working volume of 4 m$^3$. The reboiler and associated bottoms piping (not shown) provided an additional 8.3 m$^3$ of volume, for a total process fluid volume of 12.3 m$^3$. At the bottoms removal rate of 1,550 kg/hr, the resulting bottoms residence time was calculated to be approximately 8 hours.

Approximately 5,080 kg/hr of side-draw HPMAA product stream 135 was removed from Tray 7 of heavy ends column 120. The side-draw HPMAA product stream 135 comprised 99.860 wt % MAA, 0.108 wt % HIBA, 0.007 wt % MOMPA, 0.002 wt % (20 ppm) acetic acid, 0.001 wt % (7 ppm) MMA, 0.004 wt % acetone, and 0.013 wt % water, based on the total weight of the side-draw HPMAA product stream 135. Methacrylamide, acrylic acid, and methacrolein concentrations in the side-draw HPMAA product stream 135 were below detectable limits and product color measurements varied between 2 and 7 APHA. This improved, low-impurity grade of HPMAA is especially desirable for use in the production specialty MAA polymers, including ethelyene-MAA copolymers and ionomers.

It will be apparent to one of ordinary skill in the relevant art that numerous variations and modifications may be successfully made to the foregoing example of the process of the present invention. It will be recognized, for example, that an increase in the total number of trays in heavy ends column 120 will, at a constant production rate, tend to further increase the purity level of the HPMAA produced. Such changes are within the scope of the present invention.

Further, it will be recognized that changes in the flow rate of recycle stream 165 and/or reflux stream 155 might also be made to increase purity or throughput. For example, by increasing the flow rate of recycle stream 165, the purity of the product MAA may be increased, however, the throughput (i.e., the production rate of product MAA stream 135) will be simultaneously decreased. Alternatively, by decreasing the flow rate of recycle stream 165, the purity of the product MAA may be reduced, but the production rate of product methacrylic acid will be increased. From an economic standpoint, it will be appreciated that lower production rates through the same process equipment will generally increase total manufacturing cost, while higher rates will generally lower total manufacturing cost. Therefore, it is possible using the process of the present invention to balance the factors of total manufacturing cost against product purity to achieve an optimum solution for a given specialty MAA polymer application. Such optimization of purity versus manufacturing cost—and the required adjustment of associated operating parameters, such as for example steam flow to the reboiler and inhibitor addition rates—is within the ability of one of ordinary skill in the art, given the benefit of the foregoing description of the process and product of the present invention.

The present invention described herein, therefore, is well-adapted to carry out the objects and attain the ends and advantages mentioned, as well as others inherent therein. While several embodiments of the invention have been provided hereinabove, numerous changes in the details of procedures, processes, operating conditions and apparatus may be made without departing from the intent and scope of the present invention. For example, the purification process of the present invention can be successfully applied to any industrial process involving a crude MAA stream as a part of the process. These and other similar modifications will readily suggest themselves to those skilled in the art, and are intended to be encompassed within the spirit and scope of the present invention.

What is claimed is:

1. A method of preventing decomposition of 2-hydroxy-isobutyric acid (HIBA) within a methacrylic acid product stream derived from hydrolysis of acetone cyanohydrin in the presence of an acid catalyst, said product stream comprising methacrylic acid, HIBA and the acid-catalyst, said method comprising:
adding a stabilizing agent capable of neutralizing the acid catalyst to said product stream.

2. The method of claim 1 further comprising removing the neutralized acid-catalyst from said methacrylic acid product stream by filtration or distillation.

3. The method of claim 1, wherein said stabilizing agents are selected from the group consisting of ammonia, sodium hydroxide, magnesium hydroxide, and magnesium oxide.

* * * * *